United States Patent [19]

Davis et al.

[11] Patent Number: 5,288,286
[45] Date of Patent: Feb. 22, 1994

[54] ADJUSTABLE PRESSURE CAST FOR ORTHOPEDIC INJURIES

[76] Inventors: Albert D. Davis, 23054 Vanowen St., West Hills, Calif. 91307; Gregory J. Silvers, 16103 Cornuta Ave., #3, Bellflower, Calif. 90706

[21] Appl. No.: 841,314

[22] Filed: Feb. 25, 1992

[51] Int. Cl.⁵ .............................................. A61F 3/00
[52] U.S. Cl. .......................................... 602/6; 602/5; 602/13
[58] Field of Search ............... 128/846, 882, DIG. 20; 602/1, 5, 6, 13, 23, 62; 36/1.5, 88, 93, 140, 155, 164, 165

[56] References Cited

U.S. PATENT DOCUMENTS

| | | | |
|---|---|---|---|
| Re. 27,957 | 4/1974 | Larson | 128/DIG. 20 X |
| 2,531,074 | 11/1950 | Miller | 2/13 X |
| 3,186,405 | 6/1965 | Bailey et al. | 602/13 |
| 3,473,527 | 10/1969 | Spiro | 602/62 X |
| 3,610,235 | 10/1971 | Vagacs | 602/13 |
| 4,266,298 | 5/1981 | Graziano | 602/13 X |
| 4,674,479 | 6/1987 | Jennings et al. | 128/DIG. 20 X |
| 4,947,838 | 8/1990 | Giannetti | 602/23 |
| 5,125,400 | 6/1992 | Johnson, Jr. | 128/DIG. 20 X |

Primary Examiner—Robert A. Hafer
Assistant Examiner—Sam Rimell
Attorney, Agent, or Firm—John J. Posta, Jr.

[57] ABSTRACT

A device for use as a cast for orthopedic leg injuries is disclosed which has a plurality of inflatable, adjustable pressure air chambers contained within a resilient outer support casing which may easily be installed around a patient's lower extremity to control tissue edema and minor undisplaced fractures, acute sprains, and ruptures of supporting ligaments. The cast apparatus of the present invention uses three sets of air chambers to support the lower leg, the ankle, and the lower foot, respectively, of a patient. The ankle portion of the cast apparatus has special support apparatus designed to provide excellent ankle support in a unique manner. Splint members may also be used in conjunction with the cast apparatus of the present invention, with a variety of techniques being used to mount the splint members onto the cast apparatus. The device can also readily be used as a cast for upper extremities.

13 Claims, 4 Drawing Sheets

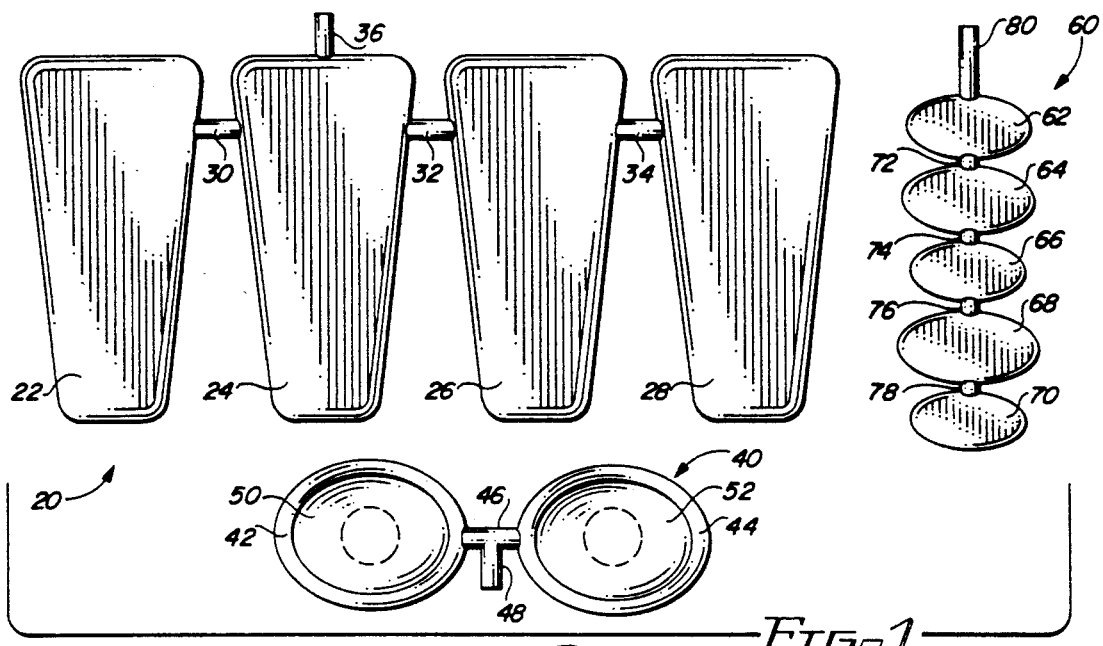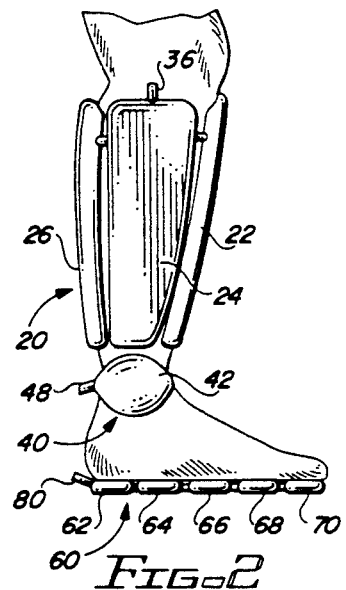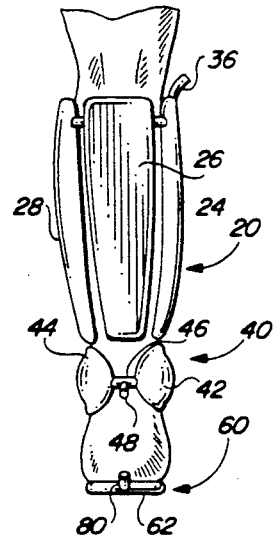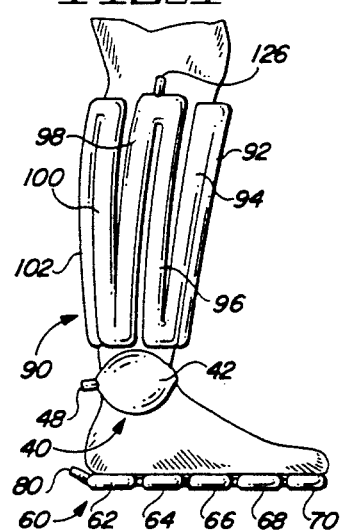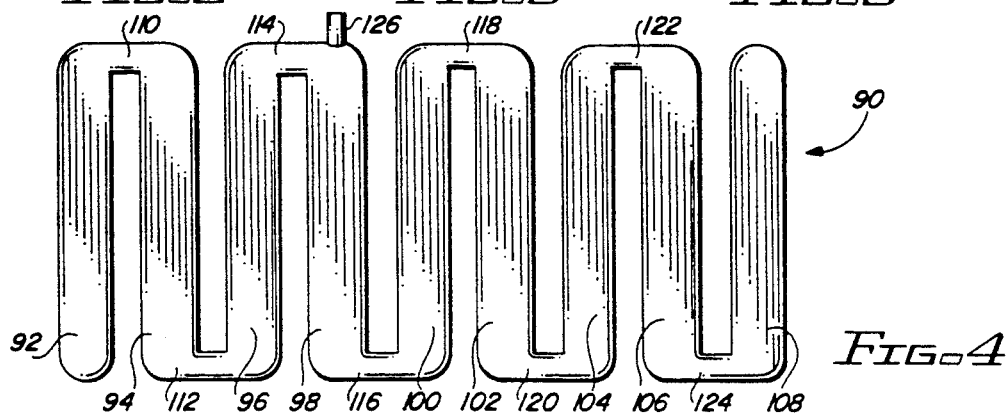

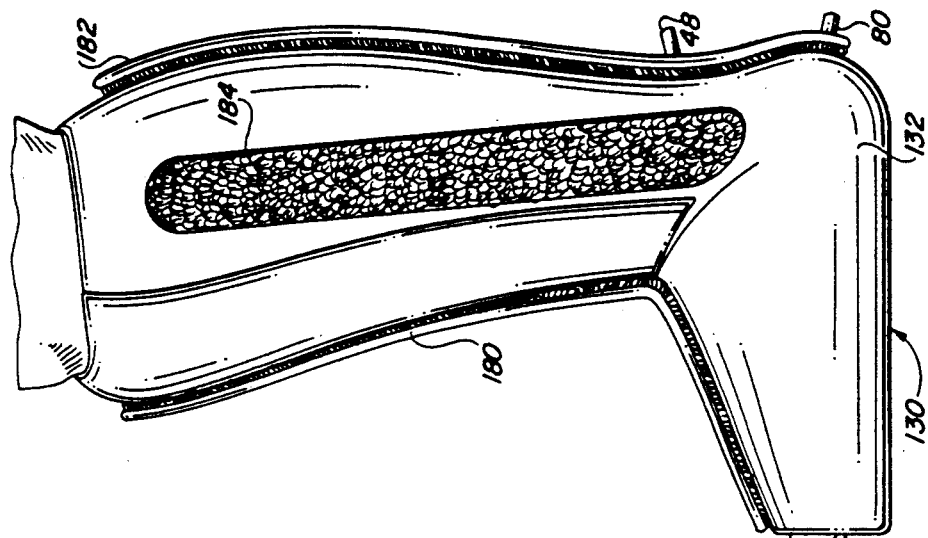
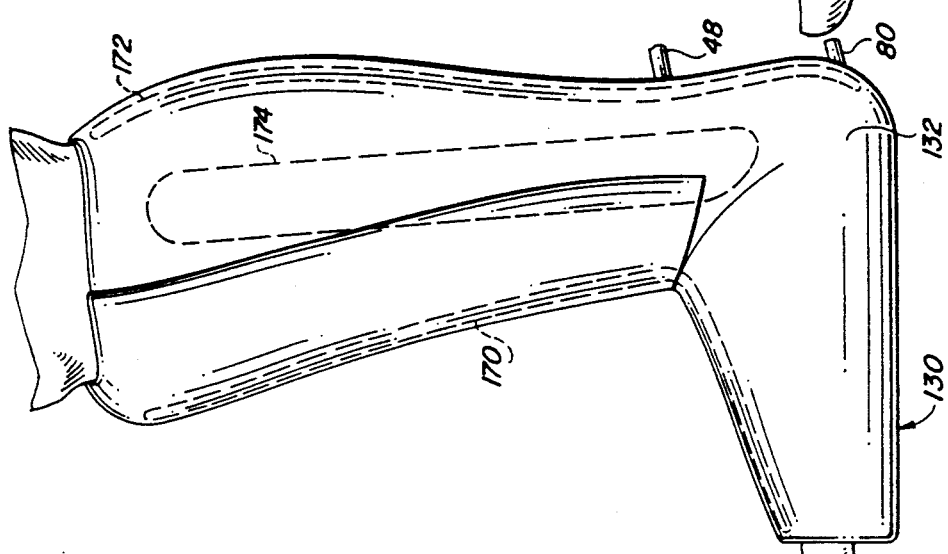
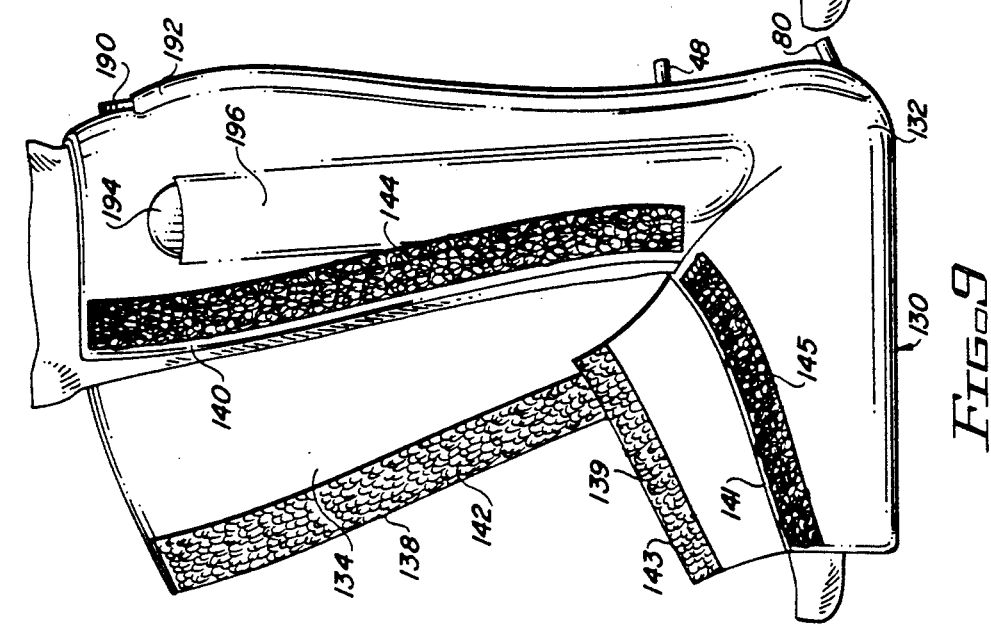

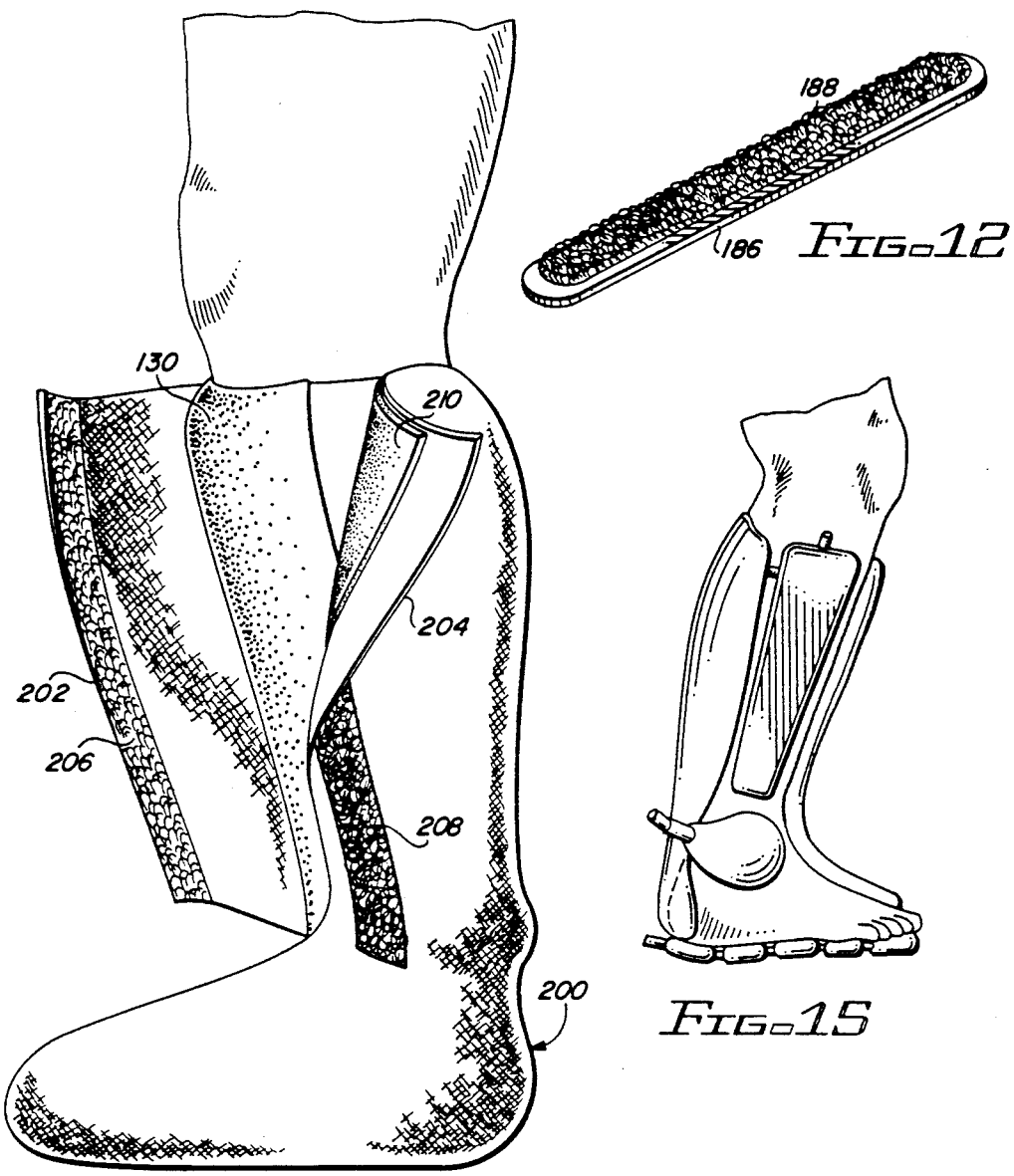
FIG-12
FIG-13
FIG-15
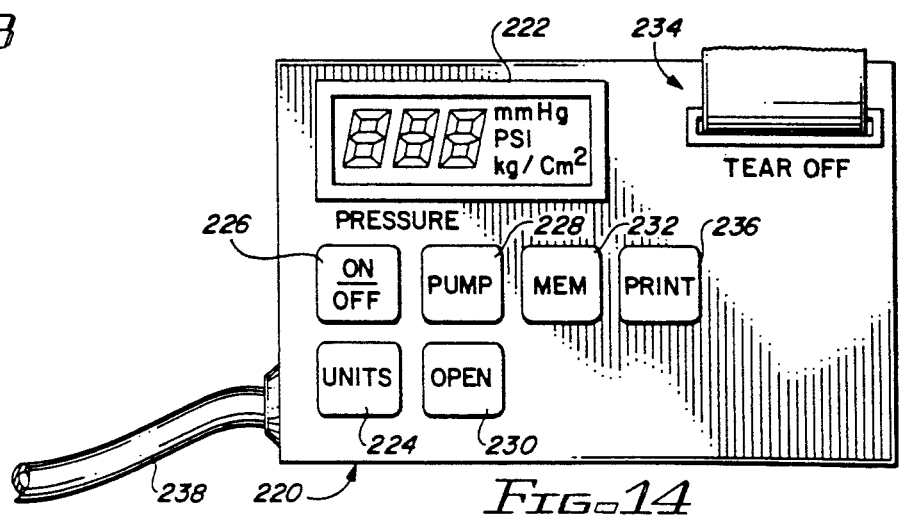
FIG-14

ADJUSTABLE PRESSURE CAST FOR ORTHOPEDIC INJURIES

BACKGROUND OF THE INVENTION

1. Field of the Invention

The present invention relates generally to a cast for orthopedic leg injuries, and more particularly to an inflatable cast having a plurality of adjustable pressure air chambers contained within a resilient outer support casing which may easily be installed around a patient's lower extremity to control tissue edema and minor undisplaced fractures, acute sprains, and ruptures of supporting ligaments.

The traditional techniques of treating orthopedic leg injuries have revolved around three type of devices: casts, which have application primarily in broken legs; splints, which are utilized to immobilize and stabilize injuries; and pressure bandages, which are used both to control swelling and to present a degree of support, particularly to ankles. Splints and elastic bandages are often used in conjunction with each other. As in other areas of medicine, creative individuals have come up with a variety of departures from these standard themes in order to present better techniques of patient treatment.

One of the first alternative devices is taught in U.S. Pat. No. 3,561,435, to Nicholson. The Nicholson apparatus is an inflatable splint which holds a cooling medium, such as crushed ice, on its interior side. The inflatable splint fits over the patients lower leg, and is inflated both to stiffen the splint and to bring the cooling interior surface of the splint into intimate contact with the patient's leg. The Nicholson device is designed to be used only temporarily rather than over an extended period.

Another variation on the theme of a cast is illustrated in U.S. Pat. No. 3,643,656, to Young et al., and in U.S. Pat. No. 4,817,590, to Stancik, Jr. These devices are both one-time inflatable casts, which are each applied in similar fashion to a patient's lower leg in a loose-fitting manner. Following the initial installation, they both have an inflatable compartment for placement adjacent the patient's leg located in the interior of the cast filled with foam to closely fit against the patient's leg.

Young et al. uses the introduction of a foam-producing substance into the inflatable compartment to provide the close fit. Stancik, Jr. injects a material which hardens in the inflatable compartment, in a manner similar to that of the Young et al. reference.

These devices have a drawback which limits their application considerably. Both the Young et al. and the Stancik, Jr. devices are essentially replacements for a fixed shape cast, in that once the foam sets they will be in a fixed configuration. Thus, their only application is as a replacement for a fixed cast, and due to their added cost and lack of additional advantages they present no substantial advantage over standard casts. Additionally, they are inapplicable in situations where there is any substantial tissue swelling. Finally, they provide no support for the ankle, other than the mere presence of the inflatable compartments.

The problem of providing a variable and changeable inner configuration is solved at least in part through the use of an inflatable cast apparatus, with air-inflated inner chambers being used to place pressure on the leg. Such devices are disclosed in U.S. Pat. No. 3,580,248, to Larson, in U.S. Pat. No. 3,786,805, to Tourin, and in U.S. Pat. No. 3,955,565, to Johnson, Jr. The Larson and Johnson, Jr. '565 devices are remarkably similar, both having front and back hard shells which are fastened together with hardware (Larson) or straps (Johnson, Jr. '565) to enclose the lower leg and foot.

The Larson device has inflatable liners in each shell half covering the entire lower leg and most of the foot, while the Johnson, Jr. '565 device has inflatable air bags in each shell half extending the length of the lower leg. They both offer little adjustment for different size legs other than the inflatable compartments, and are really designed mainly to immobilize a patient's leg. They also provide no particular support for the ankle other the mere existence of the inflatable compartments, which provide little ankle support.

Differing somewhat from these hard shell designs is the Tourin apparatus, which has more parts than any of the other devices of this type known. Rather than using hard shells, the Tourin device uses a complex frame having front and back inflatable cushions supported from a frame. Tourin suffers some of the same deficiencies as the Larson and Johnson, Jr. '565 devices, and adds substantially to these deficiencies with its complexity, undoubted high cost of manufacture, and its difficulty of assembly.

As might be expected, the art has more recently produced devices which, although completely different, do provide ankle support alone. U.S. Pat. No. 4,628,945, to Johnson, Jr. (the same Johnson, Jr. as in the '565 patent) and U.S. Pat. No. 4,977,891, to Grim are examples of ankle braces using inflatable compartments. Johnson, Jr. '945 uses shell members with inflatable, partially foam-filled liners to provide ankle support, while Grim uses an ankle brace with inflatable bladders which are pumped up when the wearer walks or runs. Both devices are only suitable for ankle support, and are not intended for the same applications as that of the present invention.

It is accordingly the primary objective of the present invention that it provide an improved cast apparatus having inflatable cushioning support for the leg of a patient. As such, it is an objective that the inflatable cushioning for the patient's leg should be adjustable in pressure at any point in time over the entire period of use by the patient to allow the pressure to be used to control edema after the initial occurrence of an injury, and to provide continuing support as the healing process continues. The mechanism for providing the pressure to the cast apparatus should be easy and convenient to use, as well as being capable of precision in its operation to precisely adjust the pressure on the patient's leg.

It is a further objective of the cast apparatus of the present invention that it provide ankle support specifically designed for the ankle instead of mere air cushions which happen to bear in part against the ankle. The ankle support apparatus must be fully integrated in the cast apparatus of the present invention, and must further be capable of pressure adjustment independently of the inflatable cushioning provided for the leg of the patient.

It is yet another objective of the cast apparatus of the present invention that it be capable of providing support and cushioning for the foot of the patient. In addition to restricting the degree of movement and providing support for the patient's foot, the cast apparatus of the present invention should also present foot cushioning allowing the patient (with the approval of his of her physician) to place weight on the leg supported by the cast apparatus of the present invention. Like the ankle support apparatus, the foot cushioning and support apparatus must be fully integrated in the cast apparatus of the present invention, and must further be capable of pressure adjustment independently of the inflatable leg cushioning and the ankle support apparatus.

It is an additional objective of the adjustable cast of the present invention that it be easy both to install and to adjust on the leg of a patient. It should also be manufacturable of lightweight, non-rigid material which is both tough and durable to afford it excellent strength and durability. It is a further objective of the cast apparatus of the present invention that it offer the ability to use one or more rigid splints if desired, with the splints being easily installable in integrated fashion into the cast apparatus. Finally, it is also an objective that all of the aforesaid advantages and objectives of the present invention be achieved without incurring any substantial relative disadvantage.

It should be noted that this invention can readily be applied to other extremities, including the arm, wrist and hand, and should not be considered as limited to a leg and foot.

SUMMARY OF THE INVENTION

The disadvantages and limitations of the background art discussed above are overcome by the present invention. With this invention, an inflatable cast having a plurality of air chambers is designed to fit on the lower leg, preferably from just below the knee to the crease of the toes. The cast apparatus of the present invention has three completely separate sets of air chambers: a first set of multiple air chambers for providing adjustable cushioning for the leg of a patient; a second set of two air chambers for supporting the ankle of a patient; and a third set of multiple air chambers for providing both support and cushioning for the foot of a patient. All three sets of air chambers are independently inflatable.

The three sets of air chambers are located and supported between an external sleeve member made of non-rigid elastomeric material and an inner lining made of soft fabric material. Extending from the external sleeve member are three air fill valves. The air fill valve for the first set of air chambers is located at the proximal end of the cast apparatus, on the lateral side thereof. The air fill valves for the second and third sets of air chambers are located in the lower posterior side of the cast apparatus, near the heel of the cast apparatus.

The anterior portion of the cast apparatus which encases the leg has a longitudinal opening there to facilitate installation of the cast apparatus on a patient's leg. In the preferred embodiment, the foot portion of the cast apparatus is open only at the rear (although in an alternate embodiment the top surface of the foot portion of the cast apparatus also has an opening therein). The cast uses a Velcro-type material (Velcro being a trademark), with mating portions mounted on the inside of the cast apparatus adjacent one side of the longitudinal opening and on the outside of the cast apparatus adjacent the other side of the longitudinal opening.

This material is essentially a male and female type of fastener, with the female portion being a strip of material with curly strands or loops of material on the outer surface, and the male portion being a strip of material with a large number of flexible resilient plastic hooks on the outer surface, as illustrated in U.S. Pat. No. 3,063,718, to Steincamp. When the male and female strips of material are pressed against one another, the hooks in the male strip become entangled with the loops in the female strip, retaining the two strips together until they are forced apart.

The mating strip on the inside of the cast apparatus adjacent the one side of the longitudinal opening is placed over the mating strip on the outside of the cast apparatus adjacent the other side of the longitudinal opening to close the cast apparatus around the leg of a patient. This arrangement allows for some degree of size adjustment depending on the relative lateral alignment of the mating strips when they are placed together. Therefore, in the preferred embodiment, the mating strips are relatively wide to allow for a relatively large degree of adjustment to allow the cast apparatus to fit legs differing to some degree in size.

The cast apparatus also contains two additional elements in its primary embodiment. First, premolded ankle cups are located on the inside of each of the two air chambers in the second set of air chambers. These premolded cups are thus located between the air chambers and the fabric lining located on the interior of the cast apparatus, and are used to support the ankle bone prominence for both the lateral and the medial ankle malleolus. Secondly, a relatively thick reinforcing pad made of dense material and extending the length of the foot is used under the third set of air chambers to protect them if the patient places weight on the leg carrying the cast apparatus.

In another aspect, the cast apparatus allows for the use of one or more splint members in conjunction with the elastomeric external sleeve member to provide additional stiffness to the cast. The splint members may be made of metal or from a lightweight but relatively stiff plastic material. The splint members may be for anterior, posterior, lateral, or medial placement; indeed, more than one splint may be utilized to provide the desired therapy.

If desired, the elastomeric external sleeve member may be molded with one or more splint members located therein. This is particularly applicable to the use of the lateral and medial splint members. In the preferred embodiment, Velcro-type mating strips are located on the exterior surface of the elastomeric external sleeve member to facilitate the attachment of splint members having mating strips adhesively affixed thereon. In yet another embodiment, the elastomeric external sleeve member may be manufactured with a plurality of pockets located therein to receive one or more splint members. Additional straps may also be utilized to retain the splints in position on the cast apparatus.

If desired, a sock may be provided to cover the cast apparatus to keep it clean. Such a sock member may be made of durable fabric such as Nylon, with Velcro-type mating strips being used to close it when it is positioned around the cast apparatus. In order to prevent movement of the sock on the cast apparatus, thin foam rubber strips may be sewn into the inside of the sock so that they will make frictional contact with the exterior of the cast apparatus when the sock is installed in place.

The three sets of air chambers each have an air fill valve, as stated above. A bulb-type pump member may be used together with a pressure gauge and a segment of tubing having a connector on the distal end thereof to fill each set of the air chambers to a desired pressure level. In an alternate embodiment, an electric pump may be used instead to fill the three sets of air chambers. Such an electric pump may have a built-in electronic pressure gauge, as well as a printer to record the pressures in the three sets of air chambers.

It may therefore be seen that the present invention teaches an improved cast apparatus having inflatable cushioning support for the leg of a patient. As such, the inflatable cushioning for the patient's leg is completely adjustable in pressure at any point in time over the entire period of use by the patient, thereby allowing the pressure to be used both to control edema after the initial occurrence of an injury, and to provide continuing support as the healing process continues. The mechanism for providing the pressure to the cast apparatus is easy and convenient to use, and is capable of precision in its operation to precisely adjust the pressure on the patient's leg.

The cast apparatus of the present invention also provides ankle support specifically designed for the ankle instead of mere air cushions which happen to bear in part against the ankle. The ankle support apparatus is fully integrated in the cast apparatus of the present invention, and further is capable of pressure adjustment independently of the inflatable cushioning provided for the leg of the patient.

The cast apparatus of the present invention additionally is capable of providing both support and cushioning for the foot of the patient. In addition to restricting the degree of movement and providing support for the patient's foot, the cast apparatus of the present invention utilizes foot cushioning allowing the patient to place weight on the leg supported by the cast apparatus of the present invention. Like the ankle support apparatus, the foot cushioning and support apparatus is fully integrated in the cast apparatus of the present invention, and further is capable of pressure adjustment independently of the inflatable leg cushioning and the ankle support apparatus.

The adjustable cast of the present invention is easy to use, both in installing it on the leg of a patient, and in adjusting it after the initial installation. It may also be manufactured of lightweight, non-rigid material which is both tough and durable to afford the cast apparatus excellent strength and durability. The cast apparatus of the present invention additionally offers the ability to use one or more rigid splints if desired, with the splints being one easily installable in integrated fashion into the cast apparatus. Finally, all of the aforesaid advantages and objectives of the present invention are achieved without incurring any substantial relative disadvantage.

DESCRIPTION OF THE DRAWINGS

These and other advantages of the present invention are best understood with reference to the drawings, in which:

FIG. 1 is a plan view of the three sets of air chambers used in the preferred embodiment, illustrating the first set of air chambers for cushioning the lower leg between the ankle and the knee, the second set of air chambers for cushioning the ankle, and the third set of air chambers for cushioning the bottom of the foot;

FIG. 2 is a schematic right side view of the three sets of air chambers shown in FIG. 1 located in the proper positions on the lower leg of a patient;

FIG. 3 is a schematic back view of the three sets of air chambers shown in FIG. 1 located in the proper positions on the lower leg of a patient;

FIG. 4 is a plan view of an alternate embodiment first set of air chambers for cushioning the lower leg between the ankle and the knee;

FIG. 5 is a schematic right side view similar to view of FIG. 2, but of the three sets of air chambers shown in FIG. 4 located in the proper positions on the lower leg of a patient;

FIG. 9 is a left side view of the cast apparatus shown in FIGS. 6 and 7, but with a plurality of splint members (shown only in part) located inside a plurality of pockets located in the elastomeric external sleeve member;

FIG. 10 is a left side view of the cast apparatus shown in FIGS. 6 and 7, but with a plurality of splint members (shown in hidden lines) located inside the elastomeric external sleeve member;

FIG. 11 is a left side view of the cast apparatus shown in FIGS. 6 and 7, but with a plurality of splint members (two of which are shown) having Velcro-type mating strips secured thereto attached to mating Velcro-type strips located on the outer surface of the elastomeric external sleeve member;

FIG. 12 is a plan view of a splint member for attachment to the cast apparatus shown in FIG. 11, showing a Velcro-type mating strip adhesively secured to one side thereof;

FIG. 13 is a left side plan view of the cast apparatus shown in FIGS. 6 and 7, with a sock member having Velcro-type mating strips to close the sock member when it is positioned around the cast apparatus, and also showing a foam rubber strip located on the inside of the sock to make frictional contact with the exterior of the cast apparatus to prevent movement of the sock on the cast apparatus; and FIG. 14 is an electric pump for use instead of the apparatus shown in FIG. 8 to fill the air chambers of the cast apparatus shown in FIGS. 6 and 7.

FIG. 15 shows a modification of one set of air chamber to show it covering the instep and heel of a foot.

DETAILED DESCRIPTION OF THE PREFERRED EMBODIMENT

Figure 8:
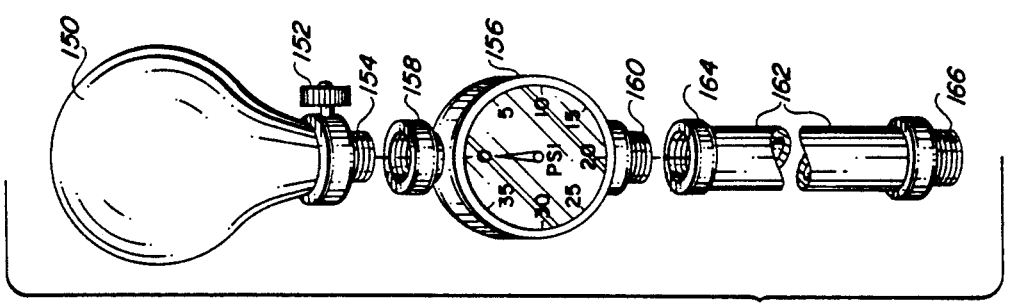
FIG. 8 is an exploded view of a bulb-type pump, a pressure gauge, and a segment of tubing having a connector at the distal end thereof, all for use in filling the air chambers of the cast apparatus shown in FIGS. 6 and 7.

The preferred embodiment of the present invention utilizes three sets of air chambers which are illustrated in FIG. 1. A first set of air chambers 20 illustrated at the top of FIG. 1 is for cushioning the lower leg of a patient between the ankle and the knee. The first set of air chambers 20 includes an anterior leg air chamber 22, a lateral leg air chamber 24, a posterior leg air chamber 26, and a medial leg air chamber 28.

Each of the leg air chambers 22, 24, 26, and 28 is approximately ten inches long, and is of decreasing width from the proximal end (near the knee) to the distal end (near the ankle). The width of each of the leg air chambers 22, 24, 26, and 28 is just less than one-quarter of the circumference of a leg. Typically, since the cast apparatus of the present invention will be used on legs of widely varying sizes, it will be made in several different sizes, and thus each of the components may vary in size according to the approximate size leg the cast apparatus is designed to fit.

The leg air chambers 22, 24, 26, and 28 are preferably made of an elastomeric material such as medical grade silicone rubber. The leg air chambers 22, 24, 26, and 28 are preferably made of flat inner and outer segments which are fastened together in a sealing manner around the edges thereof. The leg air chambers 22, 24, 26, and 28 in the preferred embodiment may have inner segments which are narrower than the outer segments to cause the leg air chambers 22, 24, 26, and 28 to curve around the leg in a manner closely fitting the leg when the leg air chambers 22, 24, 26, and 28 are inflated.

The interiors of the leg air chambers 22, 24, 26, and 28 are interconnected with short segments of tubing extending between them. A first side of the anterior leg air chamber 22 is connected to a first side of the lateral leg air chamber 24 by a segment of tubing 30. A second side of the lateral leg air chamber 24 opposite the first side of the lateral leg air chamber 24 is connected to a first side of the posterior leg air chamber 26 by a segment of tubing 32. A second side of the posterior leg air chamber 26 opposite the first side of the posterior leg air chamber 26 is connected to a first side of the medial leg air chamber 28 by a segment of tubing 34.

Extending approximately two inches above the top edge of the lateral leg air chamber 24 is an air fill valve 36 which is for use in filling the leg air chambers 22, 24, 26, and 28. The air fill valve 36 preferably has a ¼ inch valve stem, and is of standard design to allow air to pass therethrough when a filling hose is attached to the air fill valve 36. All four of the leg air chambers 22, 24, 26, and 28 may be simultaneously filled via the air fill valve 36.

Referring briefly to FIGS. 2 and 3, the first set of air chambers 20 is shown schematically as it will eventually be placed around the lower leg of a patient.

Shown in the center of FIG. 1 is a second set of air chambers 40 for cushioning the ankle of a patient on both sides thereof. The second set of air chambers 40 includes a lateral ankle air chamber 42 and a medial ankle air chamber 44. The ankle air chambers 42 and 44 are of roughly oval configuration, and are preferably made of flat inner and outer segments fastened together in a sealing manner around the edges thereof.

The ankle air chambers 42 and 44 in the preferred embodiment may have inner segments which are narrower than the outer segments to cause the ankle air chambers 42 and 44 to extend around the lateral and the medial ankle malleolus, respectively, in a concave manner to closely fit the lateral and the medial ankle malleolus, respectively, when the air chambers 42 and 44 are inflated. The ankle air chambers 42 and 44 are also preferably made of an elastomeric material such as medical grade silicone rubber.

The interiors of the ankle air chambers 42 and 44 are interconnected with a short segment of tubing 46 extending between the posterior side of the lateral ankle air chamber 42 and the posterior side of the medial ankle air chamber 44. Extending rearwardly approximately two inches from the center of the segment of tubing 46 is an air fill valve 48 which is for use in filling the ankle air chambers 42 and 44. The air fill valve 48 preferably has a ¼ inch valve stem, and is of standard design to allow air to pass therethrough when a filling hose is attached to the air fill valve 48. Both of the ankle air chambers 42 and 44 may be simultaneously filled via the air fill valve 48.

Located on the inner side of the lateral ankle air chamber 42 is a lateral premolded ankle cup 50 for placement against the lateral ankle malleolus. Similarly, located on the inner side of the medial ankle air chamber 44 is a medial premolded ankle cup 52 for placement against the medial ankle malleolus. The premolded ankle cups 50 and 52 are made of a semirigid material such as polyurethane. The premolded ankle cups 50 and 52 are of roughly oval configuration, and are of a size somewhat smaller than the size of the ankle air chambers 42 and 44. The premolded ankle cups 50 and 52 are adhesively secured to the inner sides of the ankle air chambers 42 and 44, respectively.

Referring briefly again to FIGS. 2 and 3, the second set of air chambers 40 is shown schematically as it will eventually be placed around the ankle of a patient.

Shown at the bottom of FIG. 1 is a third set of air chambers 60 for cushioning for cushioning the bottom of the foot of a patient. The third set of air chambers 60 includes a first foot air chamber 62, a second foot air chamber 64, a third foot air chamber 66, a fourth foot air chamber 68, and a fifth foot air chamber 70. The foot air chambers 62, 64, 66, 68, and 70 are each of roughly oval configuration, with the wider sides of the foot air chambers 62, 64, 66, 68, and 70 being adjacent in consecutive manner (with the first foot air chamber 62 being nearest the heel and the fifth foot air chamber 70 being nearest the toes).

The widths of the wider sides of the foot air chambers 62, 64, 66, 68, and 70 vary to accommodate the widths of a foot. The widths of the shorter sides of the foot air chambers 62, 64, 66, 68, and 70 are each approximately 1/5 of the length of a foot. The foot air chambers 62, 64, 66, 68, and 70 are preferably made of flat inner and outer segments fastened together in a sealing manner around the edges thereof. The foot air chambers 62, 64, 66, 68, and 70 are preferably made of an elastomeric material such as medical grade silicone rubber.

The interiors of the foot air chambers 62, 64, 66, 68, and 70 are interconnected with very short segments of tubing extending between them. The front side of the first foot air chamber 62 is connected to the rear side of the second foot air chamber 64 by a segment of tubing 72. The front side of the second foot air chamber 64 is connected to the rear side of the third foot air chamber 66 by a segment of tubing 74. The front side of the third foot air chamber 66 is connected to the rear side of the fourth foot air chamber 68 by a segment of tubing 76. The front side of the fourth foot air chamber 68 is connected to the fifth foot air chamber 70 by a segment of tubing 78.

Extending approximately two inches behind the rear edge of the first foot air chamber 62 is an air fill valve 80 which is for use in filling the foot air chambers 62, 64, 66, 68, and 70. The air fill valve 80 preferably has a ¼ inch valve stem, and is of standard design to allow air to pass therethrough when a filling hose is attached to the air fill valve 80. All five of the foot air chambers 62, 64, 66, 68, and 70 may be simultaneously filled via the air fill valve 80.

Referring briefly once more to FIGS. 2 and 3, the third set of air chambers 60 is shown schematically as it will eventually be placed under the foot of a patient.

Before detailing the construction of the rest of the cast apparatus of the present invention, an alternate embodiment for the first set of air chambers 20 illustrated in FIG. 4 will be discussed. An alternate first set of air chambers 90 illustrated in FIG. 4 has a plurality of leg tube sections, the interiors of which are interconnected to the interiors of adjacent leg tube sections. The alternate first set of air chambers 90 includes nine adjacent leg tube sections 92, 94, 96, 98, 100, 102, 104, 106, and 108.

Each of the leg tube sections 92, 94, 96, 98, 100, 102, 104, 106, and 108 is approximately ten inches long and approximately one inch in diameter, and if desired may be of decreasing diameter from the proximal end (near the knee) to the distal end (near the ankle). The leg tube sections 92, 94, 96, 98, 100, 102, 104, 106, and 108 are preferably made of an elastomeric material such as medical grade silicone rubber.

The interiors of the leg tube sections 92, 94, 96, 98, 100, 102, 104, 106, and 108 are interconnected with very short segments of tubing extending between them alternating between the proximal and distal ends thereof. The proximal ends of the leg tube section 92 and the leg tube section 94 are connected together by a segment of tubing 110. The distal ends of the leg tube section 94 and the leg tube section 96 are connected together by a segment of tubing 112. The proximal ends of the leg tube section 96 and the leg tube section 98 are connected together by a segment of tubing 114.

The distal ends of the leg tube section 98 and the leg tube section 100 are connected together by a segment of tubing 116. The proximal ends of the leg tube section 100 and the leg tube section 102 are connected together by a segment of tubing 118. The distal ends of the leg tube section 102 and the leg tube section 104 are connected together by a segment of tubing 120. The proximal ends of the leg tube section 104 and the leg tube section 106 are connected together by a segment of tubing 122. The distal ends of the leg tube section 106 and the leg tube section 108 are connected together by a segment of tubing 124.

Extending approximately two inches above the top of the leg tube section 98 is an air fill valve 126 which is for use in filling the leg tube sections 92, 94, 96, 98, 100, 102, 104, 106, and 108. The air fill valve 126 preferably has a ¼ inch valve stem, and is of standard design to allow air to pass therethrough when a filling hose is attached to the air fill valve 126. All nine of the leg tube sections 92, 94, 96, 98, 100, 102, 104, 106, and 108 may be simultaneously filled via the air fill valve 126.

Referring briefly to FIG. 5, the alternate first set of air chambers 90 is shown schematically as it will eventually be placed around the lower leg of a patient.

Figure 6:
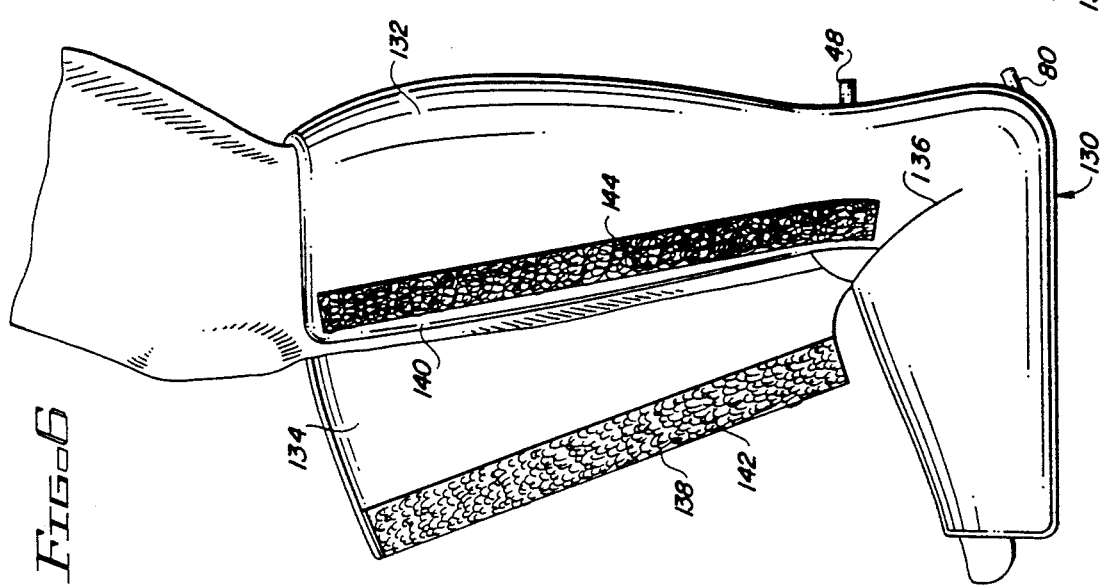
FIG. 6 is a left side view of the cast apparatus of the present invention, which encloses the three sets of air chambers shown in FIGS. 1 through 3, installed on the lower leg of a patient, but with the longitudinal opening in the anterior portion of the cast apparatus remaining open for enhanced visibility, with two Velcro-type mating strips which are used to close the longitudinal opening also shown.

Referring to FIG. 6, an assembled cast apparatus 130 is illustrated installed on the lower leg of a patient. The first set of air chambers 20 (or the alternate first set of air chambers 90), the second set of air chambers 40, and the third set of air chambers 60 are installed within the cast apparatus 130 and are not visible in FIG. 6. The first set of air chambers 20 (or the alternate first set of air chambers 90), the second set of air chambers 40, and the third set of air chambers 60 are installed in the cast apparatus 130 so that they are located around the leg of the patient in a manner similar to that illustrated in FIGS. 2 and 3 (or in FIG. 5).

The cast apparatus 130 supports the first set of air chambers 20 (or the alternate first set of air chambers 90), the second set of air chambers 40, and the third set of air chambers 60 between an external sleeve member 132 and an inner lining 134. The external sleeve member 132 is made of non-rigid elastomeric material, such as medical grade silicone rubber or natural rubber. The inner lining 134 is made of soft fabric material such as terry-cloth fabric, and is in the preferred embodiment made of 95% cotton and 5% Spandex to enable the fabric to stretch when the cast apparatus 130 is inflated. The external sleeve member 132 and the inner lining 134 are sewn together as shown to enclose the first set of air chambers 20 (or the alternate first set of air chambers 90), the second set of air chambers 40, and the third set of air chambers 60.

The portion of the external sleeve member 132 extending from just below the knee to the heel of the foot forms a tapered cylinder. The portion of the external sleeve member 132 covering the foot is boot-shaped, with the distal end being open to allow the toes to protrude therefrom. Seams 136 (one of which is shown in FIG. 6) located in both sides of the external sleeve member 132 join the leg portion of the external sleeve member 132 to the foot portion of the external sleeve member 132.

In the preferred embodiment illustrated in FIG. 6, the foot portion of the external sleeve member 132 is fully closed around the bottom, top, and sides of the foot. The foot portion of the external sleeve member 132 is thus open only at the rear to the interior of the leg portion of the external sleeve member 132, and at the front to allow the toes to protrude therefrom. The anterior portion of the leg portion of the external sleeve member 132 has a longitudinal opening there to facilitate installation of the cast apparatus 130 onto a patient's leg.

The longitudinal opening in the anterior portion of the leg portion of the external sleeve member 132 has a first edge 138 and a second edge 140. The external sleeve member 132 is sized to allow the first edge 138 to overlay the second edge 140 to close the cast apparatus 130 around the leg of the patient. When properly closed and before inflation of the first set of air chambers 20 (or the alternate first set of air chambers 90), the second set of air chambers 40, and the third set of air chambers 60, there will be approximately 5/8 of an inch of air space between the interior of the cast apparatus 130 and the leg (and also the foot) of the patient The cast apparatus 130 uses Velcro-type material to close the longitudinal opening in the anterior portion of the leg portion of the external sleeve member 132. A first mating strip 142 of the Velcro-type material is mounted on the interior of the first edge 138 of the leg portion of the external sleeve member 132 of the cast apparatus 130, adjacent one side of the longitudinal opening. A second mating strip 144 of the Velcro-type material is mounted on the exterior of the second edge 140 of the leg portion of the external sleeve member 132 of the cast apparatus 130, adjacent the other side of the longitudinal opening.

In the preferred embodiment, the mating strips 142 and 144 are each approximately 2½ inches wide by 12½ inches long. The broad widths of the mating strips 142 and 144 allow for a considerable degree of adjustment to fit legs varying somewhat in size (although the cast apparatus 130 will typically be made in several different sizes).

Extending from the cast apparatus 130 are the three air fill valves 36 (or 126), 48, and 80. The air fill valve 36 (or the air fill valve 126) for the first set of air chambers 20 (or for the alternate first set of air chambers 90) is located at the proximal end of the cast apparatus 130, on the lateral side thereof (not shown in FIG. 6). The air fill valve 48 for the second set of air chambers 40 is located in the lower posterior side of the cast apparatus 130, near the back of the ankle of the cast apparatus 130. The air fill valve 80 for the third set of air chambers 60 is also located in the lower posterior side of the cast apparatus 130, near the back of the foot of the cast apparatus 130.

Figure 7:
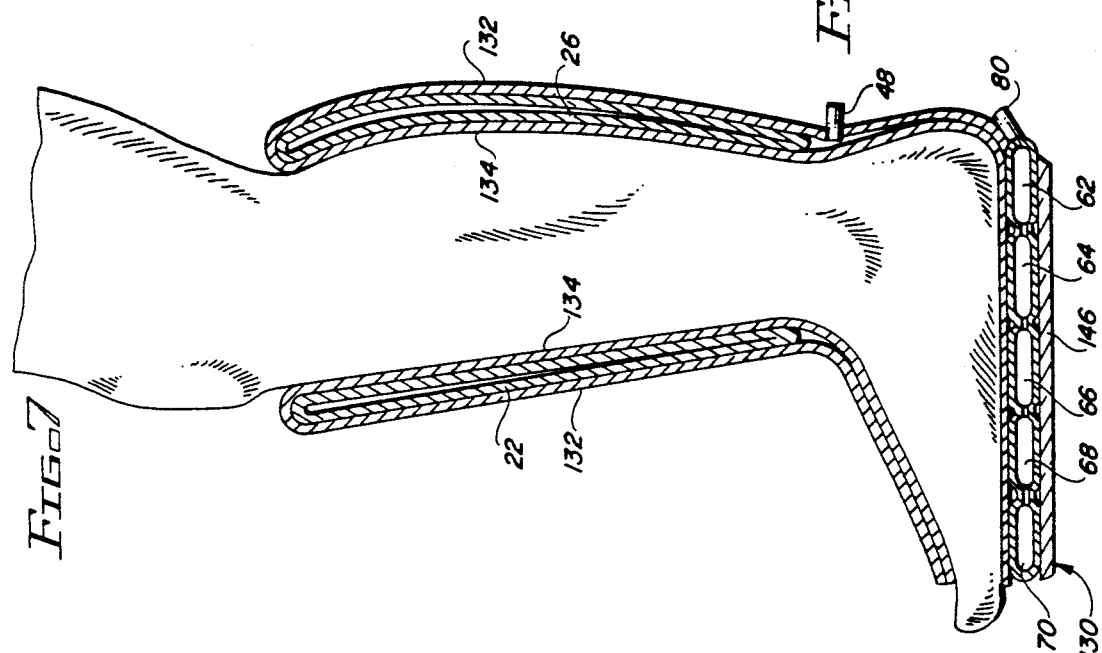
FIG. 7 is a cross-sectional view of the cast assembly shown in FIG. 6 showing the construction of the cast apparatus, including the air chambers and the cloth inner lining.

Referring now briefly to FIG. 7, the interior of the cast apparatus 130 is illustrated in a sectional view. Located on the bottom of the foot portion of the external sleeve member 132 is a dense reinforcing sole 146 which extends from the heel to the base of the toes under the bottom of the foot. The reinforcing sole 14 is approximately 1/16 inch thick, and is preferably made of synthetic rubber material.

As stated above, the first set of air chambers 20 (or the alternate first set of air chambers 90), the second set of air chambers 40, and the third set of air chambers 60 have air fill valves 36 (or 126), 48, and 80, respectively. Referring now to FIG. 8, a bulb-type pump member 150 may be used to fill the first set of air chambers 20 (or the alternate first set of air chambers 90), the second set of air chambers 40, and the third set of air chambers 60.

The bulb-type pump member 150 has a valve 152 which may be used to release pressure from the first set of air chambers 20 (or the alternate first set of air chambers 90), the second set of air chambers 40, and the third set of air chambers 60. Located at the base of the valve 152 is a male connector 154. A pressure gauge 156 is used to indicate the pressure in the first set of air chambers 20 (or the alternate first set of air chambers 90), the second set of air chambers 40, and the third set of air chambers 60. The pressure gauge 156 has a female connector 158 located on one side thereof and a male connector 160 located on the other side thereof.

A segment of tubing 162 approximately eighteen inches long has a female connector 164 located at a proximal end thereof and a air fill tube connector 166 located at a distal end thereof. The air fill tube connector 166 is designed to fit onto each of the air fill valves 36 (or 126), 48, and 80, to fill each of the first set of air chambers 20 (or the alternate first set of air chambers 90), the second set of air chambers 40, and the third set of air chambers 60, respectively, to a desired pressure level.

The pressure for each of the first set of air chambers 20 (or the alternate first set of air chambers 90), the second set of air chambers 40, and the third set of air chambers 60 typically will range between 18 PSI and 32 PSI, depending on the condition of the patient being treated. Accordingly, the pressure gauge 156 will typically read up to 40 PSI.

Referring now to FIG. 9, an alternate embodiment is illustrated which has a longitudinal opening in the top of the foot portion of the external sleeve member 132 to facilitate installation of the cast apparatus 130 onto a patient's foot. The longitudinal opening in the top of the foot portion of the external sleeve member 132 has a first edge 139 and a second edge 141. The external sleeve member 132 is sized to allow the first edge 13 to overlay the second edge 141 to close the cast apparatus 130 around the foot of the patient. When properly closed and before inflation of the third set of air chambers 60, there will be approximately ⅝ of an inch of air space between the interior of the cast apparatus 130 and the foot of the patient.

The cast apparatus 130 uses Velcro-type material to close the longitudinal opening in the top of the foot portion of the external sleeve member 132. A first mating strip 143 of the Velcro-type material is mounted on the interior of the first edge 139 of the foot portion of the external sleeve member 132 of the cast apparatus 130, adjacent one side of the longitudinal opening. A second mating strip 145 of the Velcro-type material is mounted on the exterior of the second edge 141 of the foot portion of the external sleeve member 132 of the cast apparatus 130, adjacent the other side of the longitudinal opening.

In the preferred embodiment, the mating strips 143 and 145 are each approximately 2½ inches wide by 5 inches long. The broad widths of the mating strips 143 and 145 allow for a considerable degree of adjustment to fit feet varying somewhat in size.

In another aspect of the present invention, the cast apparatus 130 preferably allows for the use of one or more splint members in conjunction with the external sleeve member 132 to provide additional stiffness to the cast apparatus 130. Splint members may be made of metal or from a lightweight but relatively stiff plastic material. The splint members may be for anterior, posterior, lateral, or medial placement; indeed, more than one splint may be utilized in conjunction with the cast apparatus 130 of the present invention in order to provide the desired therapy.

Referring now to FIG. 10, the external sleeve member 132 is illustrated to have been molded with one or more splint members located therein. Specifically, in FIG. 10 the cast apparatus 130 is illustrated with an anterior splint member 170 molded into the anterior portion of the external sleeve member 132, a posterior splint member 172 molded into the posterior portion of the external sleeve member 132, and a medial splint member 174 molded into the medial portion of the external sleeve member 132. Although it is not shown in FIG. 9, a lateral splint member could also be molded into the lateral portion of the external sleeve member 132. The technique of molding splint members into the external sleeve member 132 is particularly applicable to the use of lateral and medial splint members.

In the preferred embodiment illustrated in FIG. 11, Velcro-type mating strips are located on the exterior surface of the external sleeve member 132 to facilitate the attachment of splint members having mating strips adhesively affixed thereon. Specifically, in FIG. 11 the cast apparatus 130 is illustrated with an anterior splint member 180 attached to the anterior portion of the external sleeve member 132 with Velcro-type mating strips, a posterior splint member 182 attached to the posterior portion of the external sleeve member 132 with Velcro-type mating strips, and a first Velcro-type mating strip 184 located on the medial portion of the external sleeve member 132.

A medial splint member 186 is illustrated in FIG. 12. The medial splint member 186 has a second Velcro-type mating strip 188 on the back side thereof, which second Velcro-type mating strip 188 is for attachment to the first mating strip 184 on the medial side of the external sleeve member 132 (FIG. 11) to attach the medial splint member 186 to the medial side of the external sleeve member 132. Although it is not shown in FIG. 11, a lateral splint member could also be attached to the lateral portion of the external sleeve member 132 with Velcro-type mating strips.

In yet another embodiment, the external sleeve member 132 may be manufactured with a plurality of pockets located therein to receive one or more splint members. Referring again to FIG. 9, the external sleeve member 132 is illustrated to have been molded with one or more splint members located therein. Specifically, in FIG. 9, the cast apparatus 130 is illustrated with a posterior splint member 190 located in a pocket 192 in the posterior portion of the external sleeve member 132, and a medial splint member 194 located in a pocket 196 in the medial portion of the external sleeve member 132. Although they are not shown in FIG. 9, an anterior splint member could be located in a pocket in the anterior portion of the external sleeve member 132, and a lateral splint member could be located in a pocket in the lateral portion of the external sleeve member 132.

Additionally, straps (not shown) may also be utilized to retain splints in position on the cast apparatus 130.

If desired, a sock may be provided to cover the cast apparatus to keep it clean. Such a sock member 200 is illustrated in FIG. 13. The sock member 200 may be made of durable fabric such as Nylon. In a preferred embodiment, the sock member 200 has a longitudinal opening in the anterior portion of the leg portion of the sock member 200 to facilitate installation of the sock member 200 onto the cast apparatus 130. The longitudinal opening in the anterior portion of the sock member 200 has a first edge 202 and a second edge 204. The sock member 200 is sized to allow the first edge 202 to overlay the second edge 20 to close the sock member 200 around the cast apparatus 130.

The sock member 200 uses Velcro-type material to close the longitudinal opening in the anterior portion of the sock member 200. A first mating strip 206 of the Velcro-type material is mounted on the interior of the first edge 202 of the anterior portion of the sock member 200, adjacent one side of the longitudinal opening. A second mating strip 208 of the Velcro-type material is mounted on the exterior of the second edge 204 of the anterior portion of the sock member 200, adjacent the other side of the longitudinal opening.

In order to prevent movement of the sock member 200 on the cast apparatus 130, thin foam rubber strips 210 may be sewn into the inside of the sock member 200 so that they will make frictional contact with the exterior of the cast apparatus 130 when the sock member 200 is installed in place.

In an alternate embodiment, an electric pump 220 may be used instead of the apparatus illustrated in FIG. 8 to fill the first set of air chambers 2 (or the alternate first set of air chambers 90), the second set of air chambers 40, and the third set of air chambers 60. The electric pump 220 has a built-in electronic pressure gauge 222 which may be calibrated in different units by using a button 224.

An on/off button 226 to turn the electric pump 220 on and off, a pump button 228 to actuate the pumping mechanism in the electric pump 220, an open button 230 to release pressure, and a memory button 232 to recall a preset pressure are included in the electric pump 220. The electric pump 220 may also include a built-in printer 234 to record the pressure, which is actuated by a printer button 236. The electric pump 220 has the distal end of a segment of tubing 238 attached thereto, the proximal end of which segment of tubing 238 may be attached to a connector such as the air fill tube connector 166 (FIG. 8).

It may therefore be appreciated from the above detailed description of the preferred embodiment of the present invention that it teaches an improved cast apparatus having inflatable cushioning support for the leg of a patient. As such, the inflatable cushioning for the patient's leg is completely adjustable in pressure at any point in time over the entire period of use by the patient, thereby allowing the pressure to be used both to control edema after the initial occurrence of an injury, and to provide continuing support as the healing process continues. The mechanism for providing the pressure to the cast apparatus is easy and convenient to use, and is capable of precision in its operation to precisely adjust the pressure on the patient's leg.

The cast apparatus of the present invention also provides ankle support specifically designed for the ankle instead of mere air cushions which happen to bear in part against the ankle. The ankle support apparatus is fully integrated in the cast apparatus of the present invention, and further is capable of pressure adjustment independently of the inflatable cushioning provided for the leg of the patient.

The cast apparatus of the present invention additionally is capable of providing both support and cushioning for the foot of the patient. In addition to restricting the degree of movement and providing support for the patient's foot, the cast apparatus of the present invention utilizes foot cushioning allowing the patient to place weight on the leg supported by the cast apparatus of the present invention. Like the ankle support apparatus, the foot cushioning and support apparatus is fully integrated in the cast apparatus of the present invention, and further is capable of pressure adjustment independently of the inflatable leg cushioning and the ankle support apparatus.

The adjustable cast of the present invention is easy to use, both in installing it on the leg of a patient, and in adjusting it after the initial installation. It may also be manufactured of lightweight, non-rigid material which is both tough and durable to afford the cast apparatus excellent strength and durability. The cast apparatus of the present invention additionally offers the ability to use one or more rigid splints if desired, with the splints being easily installable in integrated fashion into the cast apparatus. Finally, all of the aforesaid advantages and objectives of the present invention are achieved without incurring any substantial relative disadvantage.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invention.

What is claimed is:

1. A cast for immobilizing and stabilizing the lower leg, comprising:
   an external sleeve member made of non-rigid elastomeric material for encasing a portion of the lower leg, said external sleeve member having a securable opening and means for releasably securing said securable opening, one end of said securable opening being located adjacent the proximal end of said external sleeve member, said securable opening being provided to facilitate installation of said cast onto the lower leg;

an inner lining located inside said external sleeve member and secured to said external sleeve member at common peripheries thereof;

inflatable first air chambers means located intermediate said external sleeve member and said inner liner for supporting a portion of the lower leg around the periphery thereof, said inflatable first air chambers means being oriented intermediate said external sleeve member and said inner liner in a manner whereby said inflatable first air chambers means extends longitudinally when said cast is installed onto the lower leg;

inflatable second air chambers means located intermediate said external sleeve member and said inner liner for applying pressure to support the ankle on both sides thereof;

wherein said inflatable first air chambers means comprise:
a) an anterior leg air chamber;
b) a lateral leg air chamber;
c) a posterior leg air chamber; and
d) a medial leg air chamber;

said cast including:
a) a first segment of tubing connecting a first side of said anterior leg air chamber to a first side of said lateral leg air chamber;
b) a second segment of tubing connecting a second side of said lateral leg air chamber opposite said first side of said lateral leg air chamber to a first side of said posterior leg air chamber;
c) a third segment of tubing connecting a second side of said posterior leg air chamber opposite said first side of said posterior leg air chamber to a first side of said medial leg air chamber; and
d) an air fill valve extending approximately two inches above the top edge of one of said anterior, lateral, posterior, and medial leg air chambers for use in filling said anterior, lateral, posterior, and medial leg air chambers.

2. A cast for immobilizing and stabilizing the lower leg, comprising:

an external sleeve member made of non-rigid elastomeric material for encasing a portion of the lower leg, said external sleeve member having a securable opening and means for releasably securing said securable opening, one end of said securable opening being located adjacent the proximal end of said external sleeve member, said securable opening being provided to facilitate installation of said cast onto the lower leg;

an inner lining located inside said external sleeve member and secured to said external sleeve member at common peripheries thereof;

inflatable first air chambers means located intermediate said external sleeve member and said inner liner for supporting a portion of the lower leg around the periphery thereof, said inflatable first air chambers means being oriented intermediate said external sleeve member and said inner liner in a manner whereby said inflatable first air chambers means extends longitudinally when said cast is installed onto the lower leg;

inflatable second air chambers means located intermediate said external sleeve member and said inner liner for applying pressure to support the ankle on both sides thereof;

wherein said inflatable second air chambers comprises:
a lateral ankle air chamber;
a lateral premolded ankle cup for placement against the lateral ankle malleolus, said lateral premolded ankle cup being adhesively secured to the inner side of said lateral ankle air chamber; and
a medial ankle air chamber;
a medial premolded ankle cup for placement against the medial ankle malleolus, said medial premolded ankle cup being adhesively secured to the inner side of said medial ankle air chamber.

3. A cast as defined in claim 2, wherein said lateral and medial ankle air chambers are made of an elastomeric rubber material, are each of an oval configuration, and are made of flat inner and outer segments fastened together in a sealing manner around the edges thereof.

4. A cast as defined in claim 2, wherein said lateral and medial premolded ankle cups are made of a semi-rigid material such as polyurethane, are each of an oval configuration, and are of a size smaller than the size of said lateral and medial ankle air chambers.

5. A cast as defined in claim 2, additionally comprising:
a segment of tubing interconnecting said lateral and medial ankle air chambers; and
an air fill valve extending from said segment of tubing for use in filling said lateral and medial ankle air chambers.

6. A cast for immobilizing and stabilizing the lower leg, comprising:

an external sleeve member made of non-rigid elastomeric material for encasing a portion of the lower leg, said external sleeve member having a securable opening and means for releasably securing said securable opening, one end of said securable opening being located adjacent the proximal end of said external sleeve member, said securable opening being provided to facilitate installation of said cast onto the lower leg;

an inner lining located inside said external sleeve member and secured to said external sleeve member at common peripheries thereof;

inflatable first air chambers means located intermediate said external sleeve member and said inner liner for supporting a portion of the lower leg around the periphery thereof, said inflatable first air chambers means being oriented intermediate said external sleeve member and said inner liner in a manner whereby said inflatable first air chambers means extends longitudinally when said cast is installed onto the lower leg;

inflatable second air chambers means located intermediate said external sleeve member and said inner liner for applying pressure to support the ankle on both sides thereof; and a sock member for use in covering said cast, said sock having a securable longitudinal opening in the anterior portion of the leg portion of said sock member to facilitate installation of said sock member on said cast, said sock member also having a plurality of thin foam rubber strips sewn into the inside of said sock member to make frictional contact with the exterior of said cast apparatus when said sock member is installed in place on said cast.

7. A cast for immobilizing and stabilizing the lower leg, comprising:

an external sleeve member made of non-rigid elastomeric material for encasing a portion of the lower leg, said external sleeve member having a securable opening and means for releasably securing said securable opening, one end of said securable opening being located adjacent the proximal end of said external sleeve member, said securable opening being provided to facilitate installation of said cast onto the lower leg;

an inner lining located inside said external sleeve member and secured to said external sleeve member at common peripheries thereof;

inflatable first air chambers means located intermediate said external sleeve member and said inner liner for supporting a portion of the lower leg around the periphery thereof, said inflatable first air chambers means being oriented intermediate said external sleeve member and said inner liner in a manner whereby said inflatable first air chambers means extends longitudinally when said cast is installed onto the lower leg;

inflatable second air chambers means located intermediate said external sleeve member and said inner liner for applying pressure to support the ankle on both sides thereof; and splint means for attachment to said external sleeve member to provide additional support to the leg.

8. A cast as defined in claim 7, wherein said splint means comprises:

at least one splint member molded into said external sleeve member.

9. A cast as defined in claim 7, wherein said external sleeve member has at least one pocket located therein, and wherein said splint means comprises:

at least one splint member for installation into said at least one pocket in said external sleeve member.

10. A cast as defined in claim 7, additionally comprising:

means for securing said splint means to the exterior of said external sleeve member.

11. A cast as defined in claim 10, wherein said splint means comprises:

at least one splint member; and wherein said securing means comprises:

a first Velcro-type mating strip located on the exterior of said external sleeve member; and a second Velcro-type mating strip located on one side of said at least one splint member.

12. A cast for immobilizing and stabilizing the lower leg, comprising:

an external sleeve member made of non-rigid elastomeric material for encasing a portion of the lower leg, said external sleeve member having a securable opening and means for releasably securing said securable opening, one end of said securable opening being located adjacent the proximal end of said external sleeve member, said securable opening being provided to facilitate installation of said cast onto the lower leg;

an inner lining located inside said external sleeve member and secured to said external sleeve member at common peripheries thereof;

inflatable first air chambers mean located intermediate said external sleeve member and said inner liner for supporting a portion of the lower leg around the periphery thereof, said inflatable first air chambers means being oriented intermediate said external sleeve member and said inner liner in a manner whereby said inflatable first air chambers means extends longitudinally when said cast is installed onto the lower leg;

inflatable second air chambers means located intermediate said external sleeve member and said inner liner for applying pressure to support the ankle on both sides thereof;

inflatable third air chambers means located intermediate said external sleeve member and said inner liner for supporting and cushioning the bottom of the foot; and splint means for attachment to said external sleeve member to provide additional support to the leg.

13. The cast as defined in claim 1 wherein a first portion of said first air chamber means extends below the ankle to cover the instep of the foot and a second portion of said first air chamber means extends below the ankle to cover the heel.

* * * * *